United States Patent [19]

Little et al.

[11] 4,105,707
[45] Aug. 8, 1978

[54] COMBINATION ALKYLATION-REFORMING PROCESS

[75] Inventors: Donald M. Little; Paul D. Hann, both of Bartlesville, Okla.

[73] Assignee: Phillips Petroleum Company, Bartlesville, Okla.

[21] Appl. No.: 739,904

[22] Filed: Nov. 8, 1976

[51] Int. Cl.² .................................................. C07C 3/54
[52] U.S. Cl. .................................................. 260/683.48
[58] Field of Search .................... 260/683.48, 683.62, 260/683.58; 208/79, 133, 141, 85, 138

[56] References Cited

U.S. PATENT DOCUMENTS

| | | | |
|---|---|---|---|
| 2,275,377 | 3/1942 | Frey ................................ | 260/683.62 |
| 2,404,050 | 7/1946 | Gilbert ................................ | 208/133 |
| 2,509,028 | 5/1950 | Abrams et al. ....................... | 208/141 |
| 2,983,773 | 5/1961 | Ballard et al. ...................... | 260/683.62 |
| 3,502,569 | 3/1970 | Hervert ................................ | 208/141 |
| 3,558,479 | 1/1971 | Jacobson et al. ..................... | 208/141 |
| 3,793,264 | 2/1974 | Chapman ........................... | 260/683.4 |
| 4,006,074 | 2/1977 | Erickson ............................. | 208/138 |

Primary Examiner—George Crasanakis

[57] ABSTRACT

High octane number motor fuel is produced by a combination process comprising alkylating isobutane with an olefin to produce an alkylate, fractionating the alkylate to remove isobutane, $C_3$ hydrocarbons and lighter, and subjecting the total alkylate to reforming to increase aromatic content thereof and yield a reformed alkylate product of improved gasoline characteristics.

10 Claims, 1 Drawing Figure

U.S. Patent
Aug. 8, 1978
4,105,707
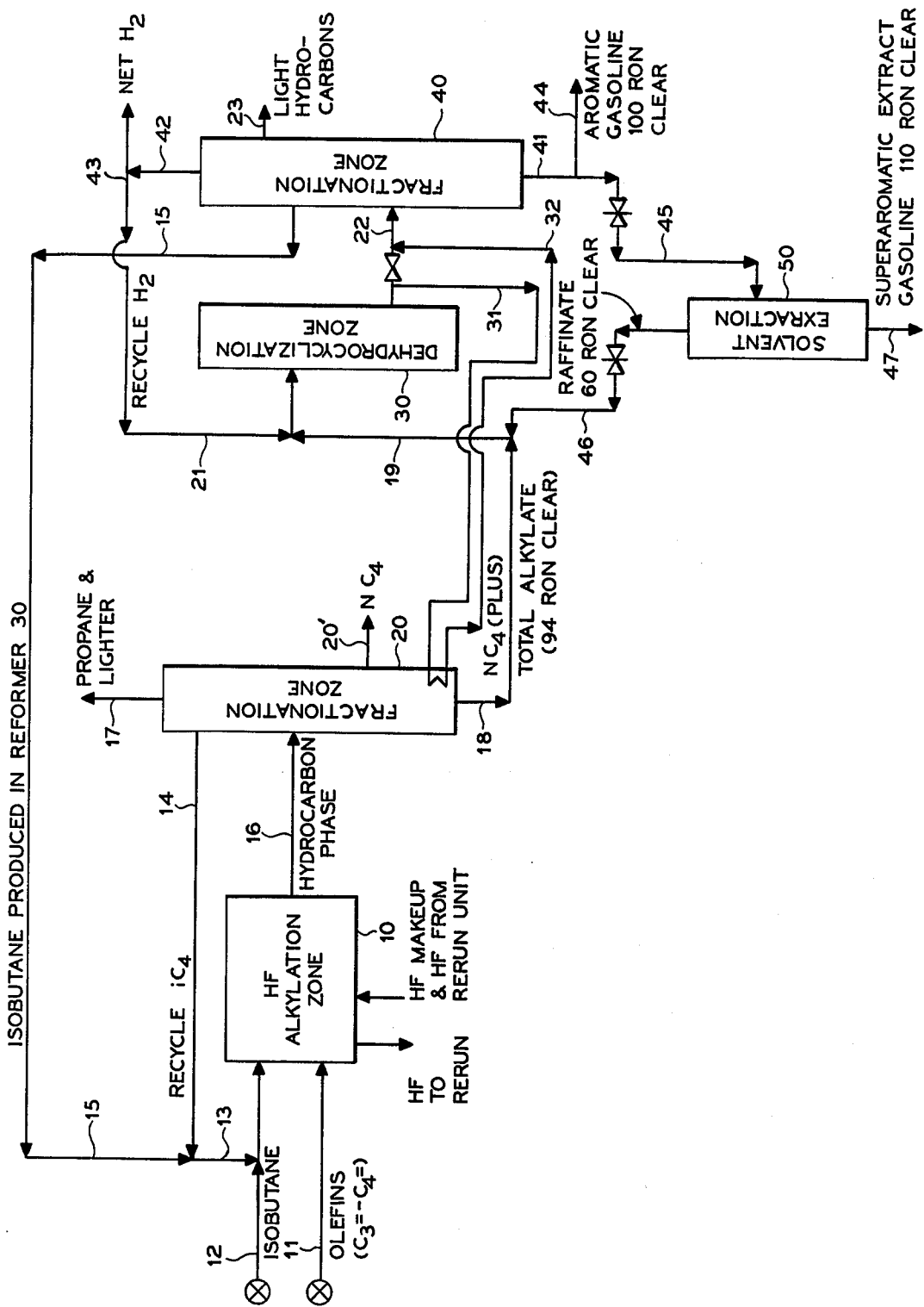

COMBINATION ALKYLATION-REFORMING PROCESS

This invention relates to the production of high octane gasoline. In accordance with one aspect, this invention relates to a combination process involving alkylation and reforming wherein the total alkylate product obtained from alkylation is reformed to increase the aromatic content. In accordance with another aspect, this invention relates to a combination process comprising alkylating isobutane with an olefin, fractionating the alkylate product to remove materials having lower boiling points than normal butane, and subjecting the total alkylate, including at least a portion of the normal butane, to reforming to increase the aromatic content of the alkylate, as well as isomerize the normal butane to isobutane which can be recycled to alkylation. In accordance with a further aspect, this invention relates to a process of upgrading alkylate gasoline having a (TEL) tetraethyl lead-free Research Octane Number (RON) of about 92–94 to a highly aromatic gasoline having a TEL-free RON of at least about 100 by reforming the total produced alkylate which alkylate includes at least a portion of normal butane and includes higher boiling materials and recovering a reformed alkylate product of improved gasoline characteristics having an increased aromatic content and octane number.

The production of motor fuels having high octane numbers and antiknock properties suitable for use in automotive and aviation fuels is of considerable importance to the refinery industry. In addition, there is an everincreasing need of TEL-free high octane number motor fuel. A common source of high octane number motor fuels is the catalytic alkylation of isoparaffin with olefin. These processes typically produce a motor fuel alkylate having a research clear octane rating of 92–94. It is also known that various refinery streams can be subjected to reforming in order to increase the aromatic content of the treated stream. We have now conceived that by combining alkylation and reforming, as is done herein, it is possible to upgrade alkylate gasoline to at least about 100 RON TEL-free by subjecting the total alkylate to reforming.

Accordingly, an object of this invention is to provide an improved alkylation operation.

It is a further object of this invention to provide an improved reforming operation.

It is a further object of this invention to provide a combination alkylation-reforming process.

A further object of this invention is to provide an improved process whereby high octane TEL-free gasoline is produced.

Other objects, aspects, and the several advantages of the invention will become apparent to those skilled in the art upon a study of the disclosure, the drawing, and the appended claims.

In accordance with the invention, the hydrocarbon effluent phase removed from an alkylation is fractionated at to remove isobutane and lower boiling materials, and the total alkylate obtained from the effluent is subjected to reforming to increase the aromatic content thereof, and thereby yield a product of improved gasoline characteristics.

In accordance with one embodiment, high octane motor fuel is produced by alkylating isobutane with an olefin to produce an alkylate, fractionating the alkylate to remove isobutane and lower boiling materials, and subjecting the remainder or total alkylate to reforming to increase aromatic content and increase the TEL-free Research Octane Number of the produced alkylate to at least about 100.

In accordance with one specific embodiment of the invention, isobutane is alkylated with a $C_3$–$C_4$ mixture of olefins to produce an alkylate product followed by fractionation of the alkylate product to remove isobutane and lower boiling material and then subjecting the remainder of the produced alkylate, including normal butane, to reforming under conditions of dehydrocyclization and isomerization to increase the aromatic content of the produced alkylate and isomerize normal butane to isobutane, and recovering a reformed alkylate product of improved gasoline characteristics.

In further embodiments, isobutane separated from the alkylation zone effluent and isobutane produced during reforming can be recycled to the alkylation as at least part of the feed therefor.

In a further embodiment, the reforming zone effluent is subjected to fractionation and solvent extraction to produce a superaromatic high octane gasoline which can have a TEL-free Research Octane Number of about 110.

The alkylation step of the present invention can be any one of a number of alkylation processes well known in the art. The alkylation can be carried out at a temperature in the range of about 0° F to about 200° F, a pressure ranging from atmospheric to about 50 atmospheres, a catalyst to hydrocarbon volume ratio of 0.5:1 to 10:1, an isobutane to olefin mole ratio of 2:1 to 20:1, and an acid-type alkylation catalyst such as sulfuric acid or hydrofluoric acid. Hydrogen fluoride is generally preferred as the catalyst.

The preferred hydrocarbon feed charged to alkylation is an olefinisoparaffin (e.g., isobutane and/or isopentane) hydrocarbon stream, preferably butylenes-isobutane. However, other olefins including mixtures of olefins can be used, such as $C_3$–$C_4$ olefin mixtures. The alkylation step of the process of this invention comprises contacting a hydrocarbon feedstock containing isobutane and olefin, preferably with an acid-acting alkylation catalyst in an alkylation zone. The isobutane and olefin(s) can be introduced as separate feedstreams or in admixture with one another. The contacting is preferably effected by intimately mixing the hydrocarbons with a catalyst, preferably a strong acid catalyst, and then passing the alkylation effluent to a phase separation zone to separate an acid phase and a hydrocarbon phase. A typical HF alkylation is disclosed in U.S. Pat. No. 3,213,157.

The reforming step of the present invention can be any one of a number of reforming processes well known in the art. Reforming can be effected at temperatures in the range of 700° F to 1100° F, a pressure of atmospheric to 1,000 psig, a liquid hourly space velocity, LHSV (volumes/volume catalyst/hr.), of 0.1 to 10, a hydrogen to hydrocarbon mole ratio of 1:1 to 20:1, in the presence of a noble metal catalyst. In actual operation, the produced alkylate preferably including normal butane obtained from the effluent of the alkylation zone is passed through a reforming zone wherein the lower octane constituents in the alkylate are converted to higher octane components by dehydrocyclization, isomerization, and the like, and other various reactions which occur in a reforming zone.

Suitable reforming catalysts can include noble metal catalysts, particularly platinum-containing catalysts, as is well known in the art. Other catalysts that can be employed include (such as those disclosed in U.S. Pat. No. 3,957,688; U.S. Pat. No. 3,894,110; U.S. Pat. No. 3,844,935; U.S. Pat. No. 3,434,960; U.S. Pat. No. 3,415,737; U.S. Pat. No. 3,558,477; U.S. Pat. No. 3,578,582; U.S. Pat. No. 3,679,578): platinum-rhenium on alumina; platinum-iridium-gold on alumina; platinum-tin on zinc aluminate; and the like.

The drawing illustrates one embodiment of the present invention. In the drawing, fresh isobutane in line 12 and a mixture of $C_3$ and $C_4$ olefins in line 11 are passed as feed to alkylation zone 10 which contains HF acid as catalyst. In zone 10, feed isobutane and olefins are intimately contacted with HF to produce an alkylate product, and the total reaction mixture including catalyst is ordinarily passed to a phase separation zone (not shown) wherein an acid phase is separated from a hydrocarbon phase by gravity. The acid phase can be returned to the alkylation zone or passed to a return unit and then returned to the alkylation zone.

The hydrocarbon phase separated from the alkylation effluent in line 16 is passed to fractionation zone 20 wherein the hydrocarbon phase is subjected to fractionation conditions such that isobutane, propane, and lighter materials are removed from an upper portion of the fractionation zone, the remainder of the hydrocarbon phase being removed as bottoms. Isobutane is removed from an upper portion of zone 20 by line 14 and recycled via line 13 and 12 for introduction into alkylation zone 10 as at least a portion of the feed. Propane and lighter materials are removed overhead by line 17 and passed to further processing as desired.

Fractionation zone 20 is operated under conditions including an upper temperature of about 113° F and a bottoms temperature of about 402° F under suitable conditions of pressure, e.g., 250 psia. It is to be understood that zone 20 can be one or more fractionation columns, as is known in the art.

The produced or total alkylate including normal butane is removed as bottoms from fractionation zone 20 by line 18 and passed directly via line 19 to reforming zone 30 wherein the total alkylate is subjected to reforming conditions in the presence of a suitable catalyst to increase the aromatic content of the total alkylate, as well as convert the normal butane to isobutane. Hydrogen (recycle) is also introduced into reforming zone 30 along with hydrocarbon feed introduced by line 21. Normal butane (vapor) can be withdrawn from zone 20 via line 20'; however, it is presently preferred that at least a portion of the normal butane in the alkylation effluent 16, which is charged to zone 20, be removed along with the total alkylate in line 18, and charged to zone 30 in order to produce isobutane therefrom in zone 30, and to charge this isobutane to alkylation 10.

The reformed alkylate product is removed from reforming zone 30 by way of line 22 and passed to the fractionation zone 40. At least a portion of the reforming zone effluent can be passed by way of line 31 as an indirect source of reboiler heat to fractionation zone 20 and then returned by line 32 for passage on to fractionation zone 40.

The reformed product introduced into fractionation zone 40 is subjected to fractionation conditions such that isobutane is removed from an upper portion of zone 40 by way of line 15 and recycled to alkylation zone 10 by way of lines 12 and 13. Light hydrocarbons lower boiling than isobutane are also removed from an upper portion of fractionation zone 40 by way of line 23 and passed to further processing as desired. Hydrogen and other light components are removed overhead from zone 40 by way of line 42 and a portion is recycled by way of line 21 to reforming zone 30. Net hydrogen produced can be removed by way of line 43 and passed to further use as desired.

The upgraded alkylate that has been subjected to reforming, freed of isobutane and lighter materials, is removed from a lower portion of zone 40 by line 41. If desired, the total aromatic gasoline removed from a lower portion of zone 40 can be removed by line 44 for final usage.

Fractionation zone 40 is operated at conditions of temperature and pressure such that isobutane is taken from an upper portion of the zone and higher boiling materials as bottoms. The temperature in the upper portion of the column will ordinarily be about 150° F and at the bottom of the column will be about 500° F. Suitable pressures include 100 to 200 psig. It is to be understood that zone 40 can be one or more separation vessels and fractionation columns, as is known in the art.

In a further embodiment of the invention, the aromatic gasoline removed from the bottom of fractionation zone 40 can be passed via line 45 to solvent extraction zone 50 wherein the aromatic gasoline is contacted with a suitable solvent, e.g., sulfolane, tetraethylene glycol, triethylene glycol, phenol, etc., to remove paraffinic materials therefrom. The paraffinic materials after being freed from solvent can be passed by way of line 46 and combined with the total alkylate and passed to reforming zone 30 by way of line 19. The superaromatic gasoline is removed by line 47. This gasoline can have an octane number of 110 RON clear.

The following example illustrates the invention.

EXAMPLE

An olefin mixture containing propylene and butylenes, the majority of which are butylenes, alkylates isobutane in a conventional commercial alkylation system 10, utilizing hydrogen fluoride as a catalyst. The system is maintained at alkylation conditions as follows:

| | |
|---|---|
| Temperature | 100° F |
| Pressure, psia | 150 (for liquid phase operation) |
| iC$_4$/olefin vol. ratio | 11.2/1 |
| HF/hydrocarbon volume ratio | 4/1 |
| Residence time, sec. | 30 |

The hydrocarbon phase 16 separated from the alkylation effluent is fractionated in 20 as described in connection with the drawing so as to remove propane and lighter 17 as overhead and an upper sidestream 14 of isobutane. The total alkylate, including normal butane removed as bottoms from the fractionation, is passed via 18 to a reforming zone 30.

The reforming zone is operated as set forth below:

| | |
|---|---|
| Temperature | 970° F |
| Pressure, psia | 150 |
| H$_2$/hydrocarbon mole ratio | 5 |
| V/V/Hr. (Hydrocarbon/catalyst) | 1 |

The catalyst is fixed bed platinum-rhenium on alumina (0.35 weight percent of each catalyst component).

The total alkylate 18 (after denormal butanization) removed as bottoms from fractionation zone 20 has a TEL-free Research Octane Number of 94 (RON clear).

The aromatic gasoline 41 separated from the reforming zone effluent has a TEL-free Research Octane Number of 100 (RON clear).

The compositions of the various streams are given in Table I wherein the stream numbers correspond to the conduit numbers in the drawing described hereinbefore.

TABLE I

| Stream: | Volume, Gal./Hr. | | | | | | |
|---|---|---|---|---|---|---|---|
| | 11 | 12 | 13 | 14 | 15 | 18 | 41 |
| Propane | — | 50 | 200 | 200 | — | — | — |
| Normal Butane | — | 50 | 100 | 100 | — | 50 | — |
| Isobutane | — | 810 | 10090 | 10000 | 90 | — | — |
| Propylene | 400 | — | — | — | — | — | — |
| Butylenes | 500 | — | — | — | — | — | — |
| Alkylate | — | — | — | — | — | 1500 | — |
| Reformate | — | — | — | — | — | — | 1200 |
| Total | 900 | 910 | 10390 | 10300 | 90 | 1550 | 1200 |
| RON Clear | — | — | — | — | — | 94 | 100 |

We claim:

1. A process for the production of high octane motor fuel which comprises:
   (a) alkylating in an alkylation zone isobutane and at least one olefin in the presence of an alkylation acid catalyst;
   (b) separating the alkylation effluent into a catalyst phase and a hydrocarbon phase;
   (c) fractionating said hydrocarbon phase obtained in (b) into a fraction comprising isobutane, a fraction comprising propane and lighter materials, and a total alkylate fraction which includes at least a portion of the normal butane present in said alkylation effluent;
   (d) passing all of said total alkylate fraction in (c) to a reforming zone and therein subjecting same to dehydrocyclization and isomerization reforming conditions of temperature and pressure in the presence of hydrogen and a suitable reforming catalyst to isomerize normal butane to isobutane and to dehydrocyclize isoparaffins to aromatics and thereby increase the aromatic content of said alkylate; and
   (e) recovering from step (d) isobutane and an alkylate product of improved gasoline characteristics having an increased aromatic content and an octane number (RON clear) of about 100.

2. A process according to claim 1 wherein the isobutane recovered from step (d) is charged to said alkylation zone in (a) as at least a portion of the feed therefor.

3. A process according to claim 1 wherein said fraction comprising isobutane in (c) is charged to said alkylation zone in (a) as at least a portion of the feed therefor.

4. A process according to claim 2 wherein the effluent from said reforming zone in (d) is fractionated into a fraction comprising isobutane which is charged to said alkylation zone in (a) as at least a portion of the feed therefor and said alkylate product comprising a high octane aromatic gasoline is subjected to solvent extraction to separate paraffin hydrocarbons therefrom to further increase the aromaticity and octane values of the automotive gasoline product.

5. A process according to claim 4 wherein the solvent-extracted paraffins separated from said aromatic gasoline are passed to said reforming zone in (d) as at least a portion of the feed therefor.

6. A process according to claim 1 wherein said fraction comprising isobutane in said fractionating step (c) and isobutane produced and recovered from (d) are charged to said alkylation zone in (a) as at least a portion of the feed therefor.

7. A process according to claim 1 wherein said alkylating is carried out at a temperature in the range of about 0° F to about 200° F, a pressure ranging from atmospheric to about 50 atmospheres, a catalyst to hydrocarbon volume ratio of 0.5:1 to 10:1, and an isobutane to olefin mole ratio of 2:1 to 20:1, and said alkylation catalyst is hydrogen fluoride.

8. A process according to claim 1 wherein said conditions in (d) include a temperature in the range of 700° F to 1100° F, a pressure of 0–1,000 psig, a liquid hourly space velocity of 0.1 to 10, a hydrogen to hydrocarbon mole ratio of 1:1 to 20:1, and the catalyst is a noble metal catalyst.

9. A process according to claim 2 wherein said alkylation catalyst is hydrogen fluoride, said olefin is a mixture of propylene and butylenes, and said fraction comprising isobutane in (c) and isobutane produced and separated in (d) are charged to said alkylation zone in (a) as at least a portion of the feed therefor.

10. A process according to claim 4 wherein at least a portion of the reforming zone effluent produced in (d) is used as a source of indirect reboiler heat for fractionation in step (c) and then combined with the remainder of the reforming zone effluent prior to being fractionated in step (e).

* * * * *